US012788126B2

(12) United States Patent
Barbarino et al.

(10) Patent No.: US 12,788,126 B2
(45) Date of Patent: Nov. 10, 2026

(54) COSMETIC SECUREMENT DEVICE FOR STABILIZATION AND ROTATION OF COSMETIC APPLICATOR CONFIGURED FOR USERS WITH LIMITED MOBILITY

(71) Applicant: L'OREAL, Paris (FR)

(72) Inventors: Casey Barbarino, San Anselmo, CA (US); Gregoire Charraud, Jersey City, NJ (US); Hyosik Dennis Min, Palisades Park, NJ (US)

(73) Assignee: L'OREAL, Paris (FR)

( * ) Notice: Subject to any disclaimer, the term of this patent is extended or adjusted under 35 U.S.C. 154(b) by 614 days.

(21) Appl. No.: 18/362,791

(22) Filed: Jul. 31, 2023

(65) Prior Publication Data

US 2025/0040686 A1 Feb. 6, 2025

(51) Int. Cl.
*A45D 44/00* (2006.01)
*G01P 13/00* (2006.01)
*A61B 5/11* (2006.01)

(52) U.S. Cl.
CPC .............. *A45D 44/00* (2013.01); *G01P 13/00* (2013.01); *A45D 2200/10* (2013.01); *A61B 5/1101* (2013.01)

(58) Field of Classification Search
CPC .. A45D 44/00; A45D 2200/10; A45D 40/262; G01P 13/00; A61B 5/1101
USPC .......................................................... 248/550
See application file for complete search history.

(56) References Cited

U.S. PATENT DOCUMENTS 9,427,065 B2 * 8/2016 Palmieri ................ A46B 9/021
12,396,544 B2 * 8/2025 Barbarino ................. A45F 3/00
2015/0034113 A1 * 2/2015 Yamagishi ........... A46B 13/023 132/200
2018/0311062 A1 * 11/2018 Pathak .................... G06F 3/017
2020/0085168 A1 * 3/2020 Pang .................... A61H 1/0285

(Continued)

FOREIGN PATENT DOCUMENTS

CN 116164203 A 5/2023
WO 2022/072241 A1 4/2022
WO 2024/145470 A9 7/2024

OTHER PUBLICATIONS

Preliminary Search Report and Written Opinion issued May 21, 2024, in corresponding French Patent Application No. 2311349 (with English translation of Category of Cited Documents).

(Continued)

*Primary Examiner* — Muhammad Ijaz

(74) *Attorney, Agent, or Firm* — Womble Bond Dickinson (US) LLP

(57) ABSTRACT

A cosmetic securement device for stabilization of a cosmetic applicator including a motion stabilizer handle, an adapter coupled to a first end of the motion stabilizer handle, and at least one rotational gear coupled to the adapter, wherein the motion stabilizer handle includes at least one sensor configured to detect a movement caused by a user, circuitry configured to determine a compensation movement to offset the detected movement, and at least one motion generation device configured to control a motion of the cosmetic applicator according to the determine compensation movement, wherein the adapter is configured to hold a plurality of different types of cosmetic applicators, and wherein the at least one rotational gear is configured to rotate the cosmetic applicator held by the adapter.

17 Claims, 17 Drawing Sheets

(56) References Cited

U.S. PATENT DOCUMENTS

| | | | | |
|---|---|---|---|---|
| 2022/0378172 | A1* | 12/2022 | Lee | A45D 34/042 |
| 2024/0215702 | A1* | 7/2024 | Barbarino | A45D 34/00 |
| 2024/0215703 | A1* | 7/2024 | Barbarino | A45F 5/1566 |
| 2024/0215704 | A1* | 7/2024 | Barbarino | A45D 34/04 |
| 2024/0215705 | A1* | 7/2024 | Barbarino | A45D 40/00 |
| 2024/0216159 | A1* | 7/2024 | Barbarino | A45D 34/04 |
| 2024/0218963 | A1* | 7/2024 | Barbarino | F16M 11/18 |
| 2024/0219933 | A1* | 7/2024 | Barbarino | A45D 34/04 |
| 2025/0040685 | A1* | 2/2025 | Charraud | A45D 40/12 |
| 2025/0040686 | A1* | 2/2025 | Barbarino | G01P 13/00 |
| 2025/0040687 | A1* | 2/2025 | Barbarino | A45D 34/00 |
| 2025/0040832 | A1* | 2/2025 | Barbarino | A45D 34/04 |
| 2025/0040833 | A1* | 2/2025 | Barbarino | A61B 5/1101 |
| 2025/0044318 | A1* | 2/2025 | Barbarino | G01P 13/00 |
| 2025/0044319 | A1* | 2/2025 | Barbarino | G01P 13/00 |
| 2025/0234978 | A1* | 7/2025 | Yue | A45D 34/042 |
| 2025/0332730 | A1* | 10/2025 | Feliciano | B25J 15/0042 |

OTHER PUBLICATIONS

International Search Report and Written Opinion issued Oct. 21, 2024, in International PCT Application No. PCT/US2024/040358.

* cited by examiner

COSMETIC SECUREMENT DEVICE FOR STABILIZATION AND ROTATION OF COSMETIC APPLICATOR CONFIGURED FOR USERS WITH LIMITED MOBILITY

FIELD

The present disclosure describes a system and features related to a device for modifying, mitigating, altering, reducing, compensation for, or the like, the movement of a cosmetic applicator caused by unintentional movements, tremors, limited mobility, or the like of a user.

BACKGROUND

Unintentional movements of the human body, or human tremors, can occur in individuals suffering from motion disorders or even healthy individuals. Due to these unintentional movements, a person may have difficulty in performing a task that requires care and precision, such as applying a cosmetic composition to a part of the body, such as the face, hands, or feet.

Therefore, there is a need for a solution that allows application of a cosmetic composition that is compatible with the diverse and disposable nature of cosmetic applicators.

SUMMARY

In one embodiment, the present disclosure is directed to a cosmetic securement device for stabilization of a cosmetic applicator including a motion stabilizer handle, an adapter coupled to a first end of the motion stabilizer handle, and at least one rotational gear coupled to the adapter, wherein the motion stabilizer handle includes at least one sensor configured to detect a movement caused by a user, circuitry configured to determine a compensation movement to offset the detected movement, and at least one motion generation device configured to control a motion of the cosmetic applicator according to the determine compensation movement, wherein the adapter is configured to hold a plurality of different types of cosmetic applicators, and wherein the at least one rotational gear is configured to rotate the cosmetic applicator held by the adapter.

In one embodiment, the present disclosure is directed to the cosmetic securement device, wherein each of the at least one rotational gear is configured to rotate independently of each other.

In one embodiment, the present disclosure is directed to the cosmetic securement device, wherein the adapter includes a ring-shaped component configured to hold the cosmetic applicator.

In one embodiment, the present disclosure is directed to the cosmetic securement device, wherein the at least one rotational gear is concentric with the ring-shaped component and wherein a rotational axis of the at least one rotational gear is a central axis of the ring-shaped component.

In one embodiment, the present disclosure is directed to the cosmetic securement device, wherein the at least one rotational gear is coupled to a face of the ring-shaped component.

In one embodiment, the present disclosure is directed to the cosmetic securement device, wherein the at least one rotational gear is embedded in the ring-shaped component.

In one embodiment, the present disclosure is directed to the cosmetic securement device, wherein the at least one rotational gear is actuated by an electric motor embedded in the cosmetic securement device.

In one embodiment, the present disclosure is directed to the cosmetic securement device, wherein the electric motor is coupled to the at least one rotational gear via at least one driver gear.

In one embodiment, the present disclosure is directed to the cosmetic securement device, wherein the electric motor is coupled to the at least one rotational gear via a shared belt.

In one embodiment, the present disclosure is directed to the cosmetic securement device, wherein the at least one rotational gear is actuated by the electric motor in response to actuation of a pushbutton or a switch embedded in the cosmetic securement device.

In one embodiment, the present disclosure is directed to a cosmetic securement device for stabilization of a cosmetic applicator, comprising a motion stabilizer handle; an adapter coupled to a first end of the motion stabilizer handle, the adapter including a cylindrical sheath configured to hold the cosmetic applicator; and at least one rotational gear coupled to the adapter, wherein the motion stabilizer handle includes at least one sensor configured to detect a movement caused by a user, circuitry configured to determine a compensation movement to offset the detected movement, and at least one motion generation device configured to control a motion of the cosmetic applicator according to the determined compensation movement, wherein the adapter is configured to hold a plurality of different types of cosmetic applicators, and wherein the at least one rotational gear is configured to rotate the cosmetic applicator held by the adapter.

In one embodiment, the present disclosure is directed to the cosmetic securement device, wherein the at least one rotational gear is concentric with the cylindrical sheath and wherein a rotational axis of the at least one rotational gear is a central axis of the cylindrical sheath.

In one embodiment, the present disclosure is directed to the cosmetic securement device, wherein the at least one rotational gear is coupled to a face of the cylindrical sheath.

In one embodiment, the present disclosure is directed to the cosmetic securement device, wherein the at least one rotational gear is embedded in the cylindrical sheath.

In one embodiment, the present disclosure is directed to the cosmetic securement device, wherein each of the at least one rotational gear is configured to rotate independently of each other.

In one embodiment, the present disclosure is directed to the cosmetic securement device, wherein the at least one rotational gear includes a first rotational gear coupled to a first section of the cylindrical sheath and a second rotational gear coupled to a second section of the cylindrical sheath.

In one embodiment, the present disclosure is directed to the cosmetic securement device, wherein the first section of the cylindrical sheath and the second section of the cylindrical sheath are configured to rotate independently of each other.

In one embodiment, the present disclosure is directed to a cosmetic securement device for stabilization of a cosmetic applicator, comprising a motion stabilizer handle; an adapter coupled to a first end of the motion stabilizer handle; and at least one rotational gear coupled to the adapter, wherein the motion stabilizer handle includes at least one sensor configured to detect a movement caused by a user, circuitry configured to determine a compensation movement to offset the detected movement and a rotation of the at least one rotational gear based on a type of the cosmetic applicator, and at least one motion generation device configured to control a motion of the cosmetic applicator according to the determined compensation movement, wherein the adapter is configured to hold a plurality of different types of cosmetic applicators, and wherein the at least one rotational gear is configured to rotate the cosmetic applicator held by the adapter.

In one embodiment, the present disclosure is directed to the cosmetic securement device, wherein the circuitry is configured to determine a speed of the rotation and an amount of rotation of the at least one rotational gear based on the type of the cosmetic applicator.

In one embodiment, the present disclosure is directed to the cosmetic securement device, wherein the at least one rotational gear is actuated by an electric motor and wherein the circuitry is configured to control power to the electric motor.

BRIEF DESCRIPTION OF THE DRAWINGS

A more complete appreciation of the embodiments and many of the attendant advantages thereof will be readily obtained as the same becomes better understood by reference to the following detailed description when considered in connection with the accompanying drawings, wherein.

DETAILED DESCRIPTION

The present disclosure describes a cosmetic applicator system that minimizes, modifies, mitigates, alters, reduces, compensates for, or the like unintentional movements by stabilizing, orienting, operating, controlling, etc. an applicator for a user and is also designed to be flexible to accommodate different types of commercially available cosmetic applications. The present disclosure further describes a system and features to enhance the functionality of such a cosmetic applicator system.

The basic features and operation of a motion stabilizing device for a cosmetic applicator is described in U.S. Pat. No. 11,458,062, which is incorporated herein by reference.

Figure 1:
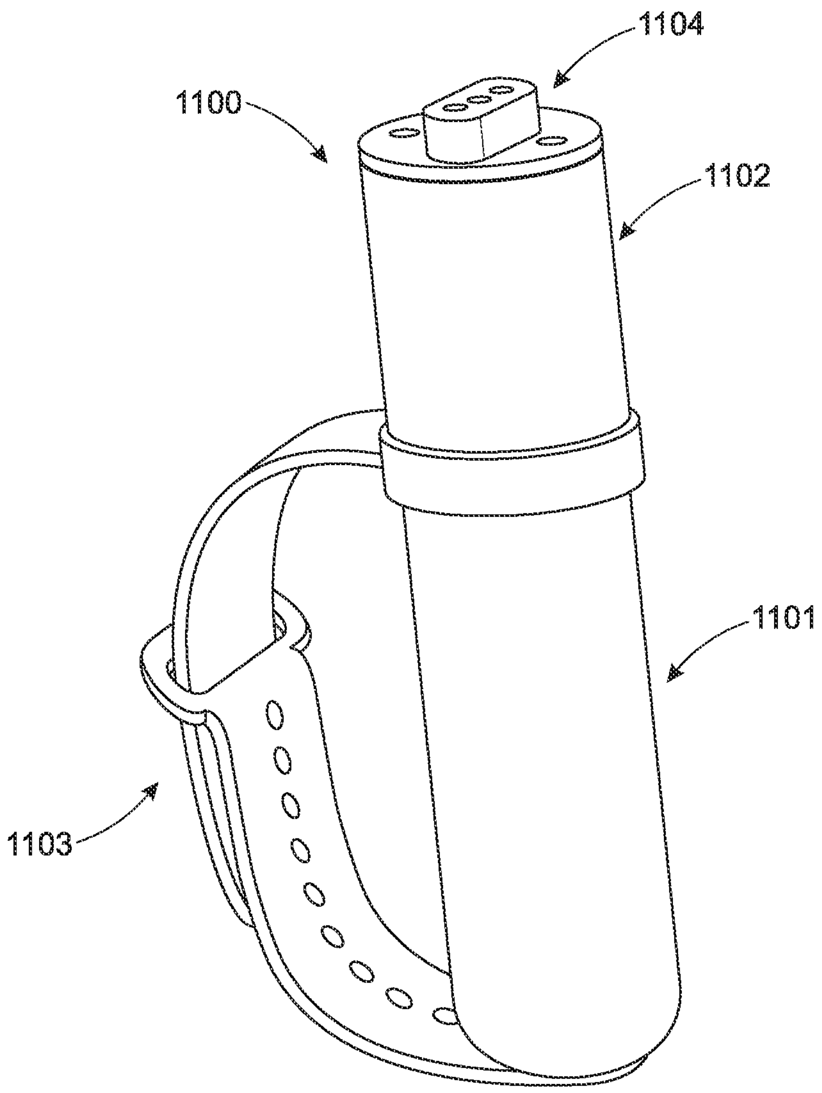
FIG. 1 shows a conventional motion stabilizing device.

FIG. 1 shows a conventional motion stabilizing device 1100, which serves as a base unit for receiving a cosmetic applicator according to an embodiment. The device 1100 includes a handle portion 1101, a receiver portion 1102 and a strap 1103. The receiver portion 1102 includes an interface 1104, shown as a male connector that couples with a cosmetic applicator, which will be discussed in detail below. The receiver portion could be utilized for communication between the base unit and the applicator. The connection to an adapter and/or an applicator could be accomplished with a mechanical coupling, such as screw-in or snap-fit, or it could be accomplished with magnets.

Figure 2:
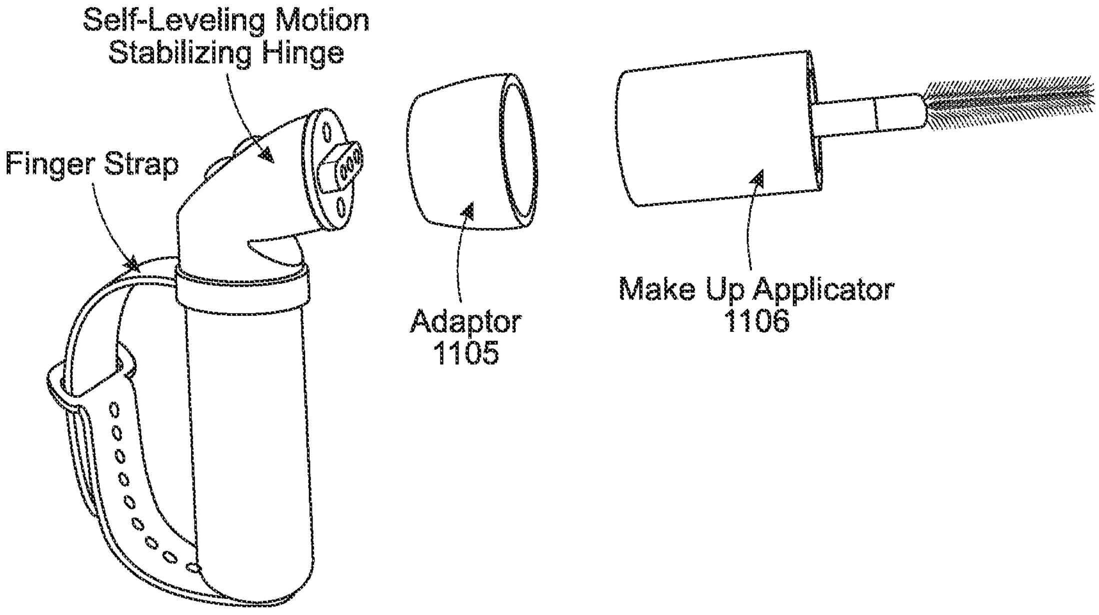
FIG. 2 shows how the conventional motion stabilizing device couples with an adapter and a make-up applicator.

FIG. 2 shows how the device 1100 couples with an adapter 1105 and a make-up applicator 1106. It can be seen that the adapter fits over the exposed end of the receiver portion 1102. The adapter includes electrical mating connectors (a female connector—not shown) in a recessed portion to make contact with the electric interface of the receiver portion 1101.

As shown in FIG. 2, the receiver portion 1102 is configured to contort, articulate, reposition, etc., between an upright posture (as shown in FIG. 1) and an angled posture (as shown in FIG. 2). This is accomplished with a hinge mechanism contained inside the receiver portion 1102. FIG. 2 shows that the hinge mechanism is a self-leveling/motion stabilizing hinge.

Figure 3A:
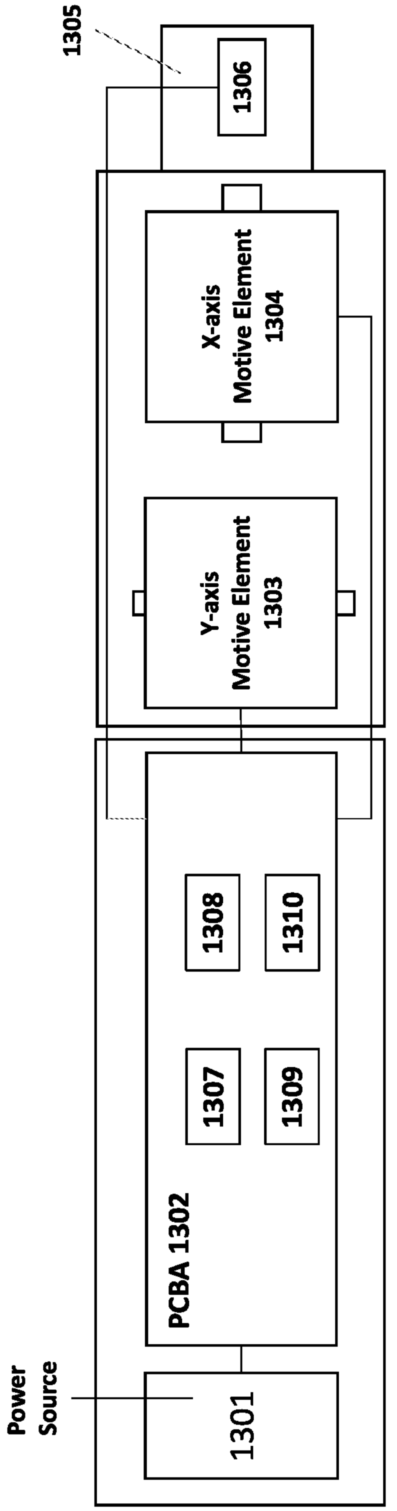
FIG. 3A shows a diagram of the internal components of a motion stabilizing device according to one embodiment.

FIG. 3A shows a diagram of the internal components of device 1100 according to one embodiment. In the handle portion, the device includes a power source 1301, which may be a battery or the like. The device includes a printed circuit board assembly (PCBA) 1302, which may include positional sensor circuitry 1307, reader circuitry 1308, control circuitry 1309, and communication interface 1310, as understood in the art.

For instance, as the sensor circuitry 1307, the PCBA may include at least one inertial sensor and at least one distributed motion sensor to detect unintentional muscle movements and measure signals related to these unintentional muscle movements that are created when a user adversely affects motion of the applicator. These sensors also detect the motion of the stabilized output relative to device. The control circuitry sends voltage commands in response to the signals to the motion generating elements (described below) to cancel the user's tremors or unintentional muscle movements. This cancellation maintains and stabilizes a position of the applicator, keeping it stable.

One of ordinary skill in the art readily recognizes that a system and method in accordance with the present invention may utilize various implementations of the control circuitry and the sensor circuitry and that would be within the spirit and scope of the present invention. In one embodiment, the control circuitry 1309 comprises an electrical system capable of producing an electrical response from sensor inputs such as a programmable microcontroller or a field-programmable gate array (FPGA). In one embodiment, the control circuitry comprises an 8-bit ATMEGA8A programmable microcontroller manufactured by Atmel due to its overall low-cost, low-power consumption and ability to be utilized in high-volume applications.

In one embodiment, the at least one inertial sensor in the sensor circuitry is a sensor including but not limited to an accelerometer, gyroscope, or combination of the two. In one embodiment, the at least one distributed motion sensor in the sensor circuitry is a contactless position sensor including but not limited to a hall-effect magnetic sensor.

The system created by the combination of the sensor circuitry, the control circuitry, and the motion generating elements may be a closed-loop control system that senses motion and acceleration at various points in the system and feeds detailed information into a control algorithm that moves the motion-generating elements appropriately to cancel the net effect of a user's unintentional muscle movements and thus stabilize the position of the applicator. The operation and details of the elements of the control system and control algorithm are understood in the art, as described in U.S. PG Publication 2014/0052275A1, incorporated herein by reference.

The communication interface 1310 may include a network controller such as BCM43342 Wi-Fi, Frequency Modulation, and Bluetooth combo chip from Broadcom, for interfacing with a network.

In the receiver portion of the device, there may be two motive elements to allow 3-dimensional movement of the receiver as anti-shaking movement. The two motive elements include a y-axis motive element 1303 and an x-axis motive element 1304, each being connected to and controlled by the PCBA 1302. Each of the motive elements may be servo motors as understood in the art. The device further includes end effector coupling 1305, which is configured to couple with the adapter 1105. The end effector coupling 1305 may include a radiofrequency identification (RFID) reader 1306, configured to read an RFID tag, which may be included with the applicator, as will be discussed below.

Figure 3B:
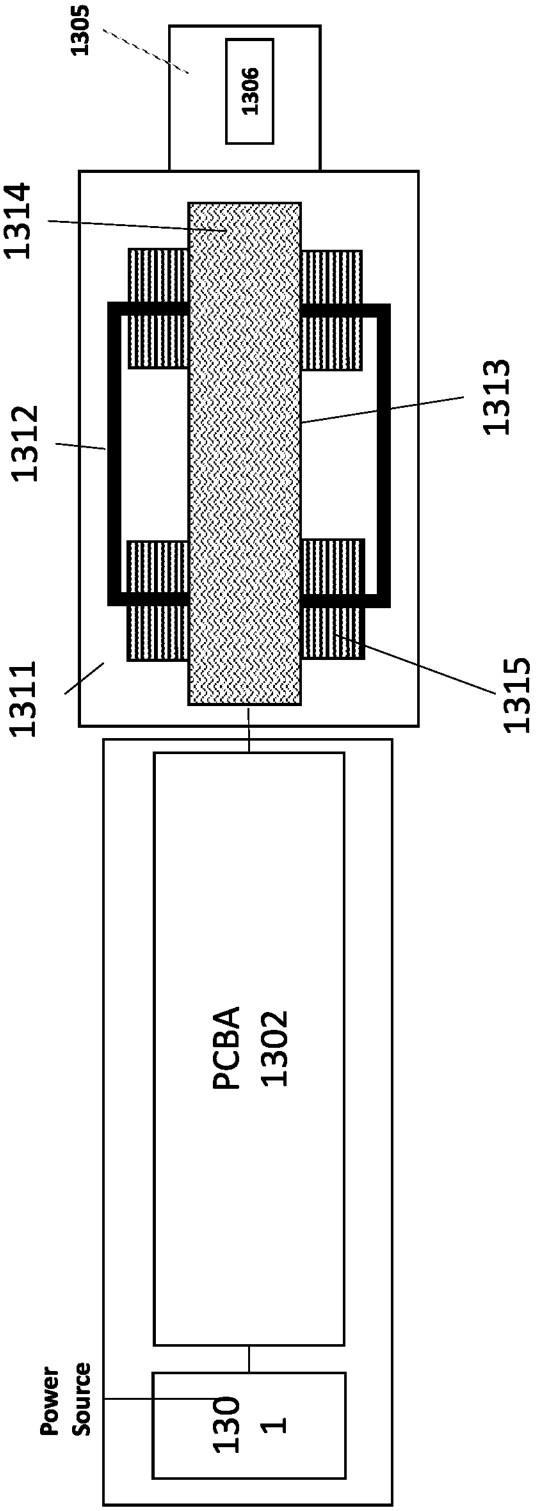
FIG. 3B shows a diagram of an alternative embodiment of the motion stabilizing device in which a receiver portion includes an electromagnetic positioner.

FIG. 3B shows a diagram of an alternative embodiment of the device 1100 in which the receiver portion includes an electromagnetic positioner 1311 instead of the motive elements shown in FIG. 3A. The electromagnetic positioner 1311 may include U-shaped magnetic cores 1312 arrayed around a non-magnetic tube 1313, which is filled with a magnetic fluid 1314. Each of the magnetic cores has arm portions that are surrounded by windings 1315. The magnetic cores may be controlled by the control circuitry in the PCBA 1302 to act as a controllable active magnetic field-generating structure which is used to generate a variable magnetic field that acts upon the magnetic fluid, causing it to be displaced, thereby enabling the armature to be moved to a desired coordinate position and/or orientation. The details of implementing the electromagnetic positioner 1311 may be found in U.S. Pat. No. 6,553,161, which is incorporated herein by reference.

In the above-described conventional motion stabilizing device, there is a problem that the interface 1104 that receives the adapter 1105 requires a specific point of attachment to align properly with the interface.

Therefore, the below embodiments provide a universal adapter connection between the handle of the motion stabilizing device in order to improve user experience and reduce the struggle and time taken to set up the system for use.

In one embodiment, the present disclosure is directed towards a cosmetic applicator. The cosmetic applicator can be used for a variety of cosmetics and cosmetic applications, including, but not limited to, mascara, eyeliner, eyebrow products, lip products (lipstick, lip gloss, lip liner, etc.), skin products, and/or hair products. In one embodiment, the cosmetic applicator can include an adapter, wherein the adapter can connect the cosmetic applicator to a motion stabilizer. The motion stabilizer can be, for example, a handle that can counteract unintentional motions such as tremors or spasms. These motions can interfere with the application of cosmetics and can also make it difficult to generally interact with cosmetic applicators or tools. For example, the many cosmetic products require a twisting motion or force to be applied to open or extrude the product. It can be difficult for users to achieve the range of motion or the precision necessary to apply these forces to the cosmetic. In one embodiment, the cosmetic applicator can hold a cosmetic and can enable the proper force to be applied to the cosmetic to open, close, mix, stir, blend, extrude, or achieve other similar functions necessary for application.

Figure 4:
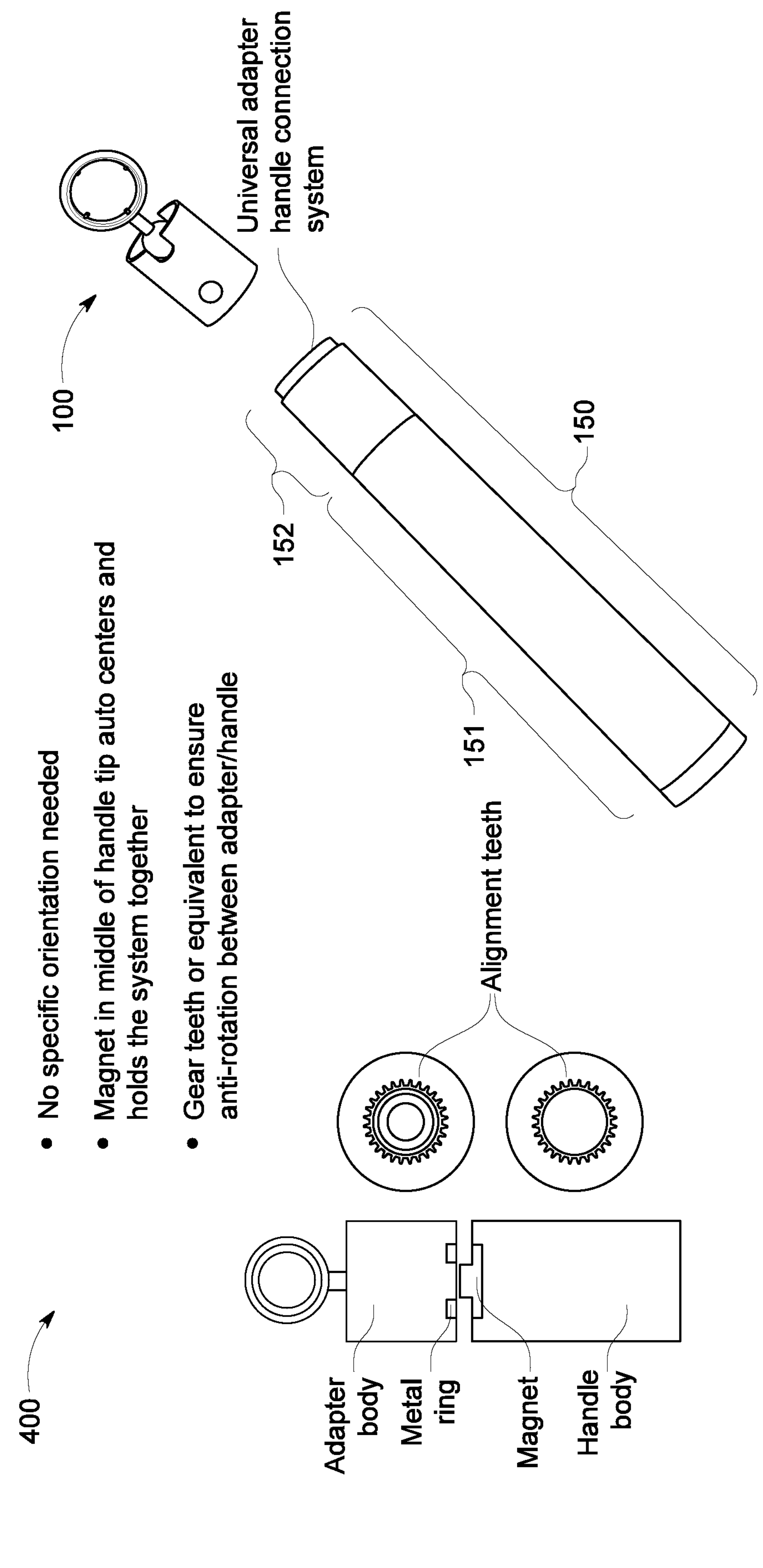
FIG. 4 shows an overview of a universal adapter handle connection system.

FIG. 4 shows an overview of a cosmetic securement device including a motion stabilizer device 150 and a cosmetic adapter 100, according to one embodiment of the present disclosure. The motion stabilizer device 150 can include at least one of a handle portion 151 and a hinge portion 152 (receiver portion). In an embodiment, the handle portion 151 is functionally similar to the handle portion 1101 shown in FIG. 1. The receiver portion 152 can be functionally similar to the receiver portion 1102 shown in FIG. 1. In an embodiment, the motion stabilizer device 150 as a whole is referred to herein as a motion stabilizer handle. In an embodiment, the cosmetic securement device includes a cosmetic adapter 100, wherein the adapter 100 can be coupled to the receiver portion 152 of the motion stabilizer device 150. In an embodiment, the cosmetic adapter 100 holds a cosmetic tool or product. In one embodiment, the cosmetic adapter 100 can be a universal adapter configured to hold different types of cosmetic products. For example, the adapter 100 can include a ring-shaped holder. Various configurations of the adapter 100 can be used for different cosmetics and tools. For example, the shape and dimensions of the cosmetic holder can be configured for different cosmetic products. The adapter 100 can be easily attached to and removed from the motion stabilizer device. The basic features and operation of the cosmetic securement device of FIG. 4 are described in co-pending U.S. patent application Ser. Nos. 18/091,882; 18/091,920; 18/091,843; 18/091,925; 18/148,957; and Ser. No. 18/148,880; and Ser. No. 18/148,930, which are incorporated herein by reference.

In one embodiment, the adapter 100 is coupled to the receiver portion 152 of the motion stabilizer device 150 via a magnetic attachment. The base or bottom end of the adapter 100 can form a chamber that can fit over a projection at the tip of the receiver portion 152. The base of the adapter can include at least one magnet, wherein the at least one magnet can be attracted to and attach to a magnet in the receiver portion 152. In one embodiment, the chamber formed at the base of the adapter 100 can fit over the receiver portion 152 in more than one orientation. The chamber can be a hollow area within the body of the adapter that is fully contained by the walls of the adapter 110. The chamber can be approximately conical in shape. In one embodiment, the chamber is cylindrical. The chamber can be configured to fit over a projection on one end of the motion stabilizer. The chamber can be used to align and guide the attachment of the cosmetic applicator to the motion stabilizer. The fit of the chamber over and around the projection on the end of the motion stabilizer limits lateral motion that would misalign the cosmetic applicator and the motion stabilizer. It can be easier for a user to align the chamber over the end of the motion stabilizer than it would be for the user to align the edges of a circular face of the adapter with the edges of a circular face of the motion stabilizer. The chamber can have rotational symmetry such that the cutout can be placed over the end of the motion stabilizer in any orientation or at any degree of rotation around the axis of the chamber. In one embodiment, the bottom end of the adapter body can include additional physical structures that can align, guide, and fix the adapter to the motion stabilizer.

Figure 5A:
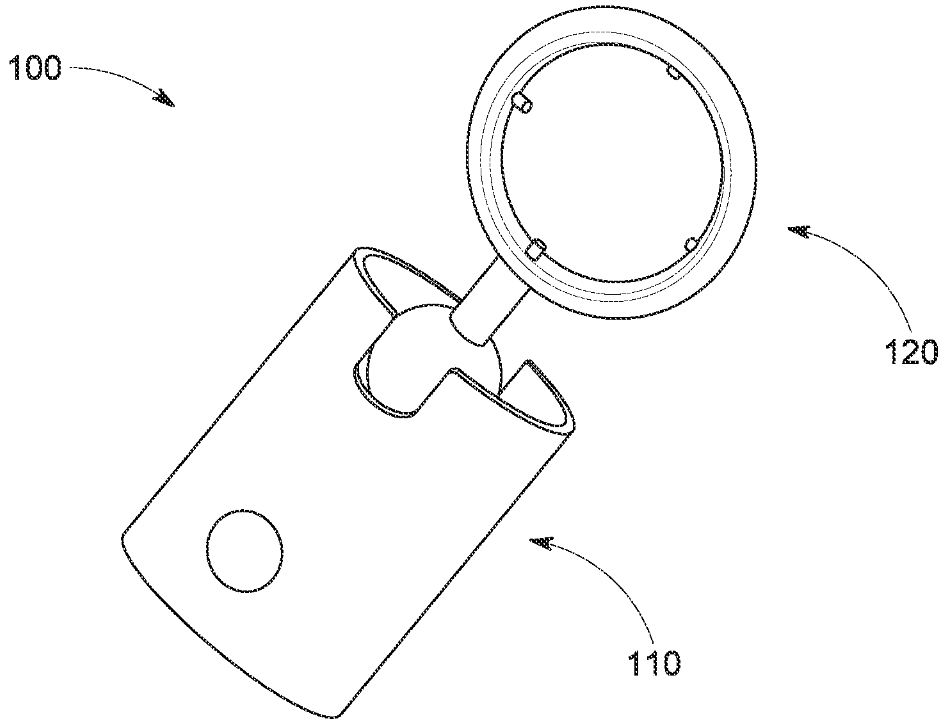
FIG. 5A shows an illustration of an adapter, according to one embodiment.

FIG. 5A shows an illustration of adapter 100, according to one embodiment of the present disclosure. The adapter 100 can include an adapter body 110, wherein the adapter body 110 can be connected to the motion stabilizer 150. The adapter body 110 can be connected to or can form the base or body of a cosmetic holder 120. Each of these components will be discussed in further detail herein. Various configurations of the adapter 100 can be used for different cosmetics and tools. For example, the shape and dimensions of the cosmetic holder 120 can be configured for different cosmetic products. The adapter 100 can be easily attached to and removed from the motion stabilizer, as will be discussed herein. In one embodiment, the adapter 100 can broaden the range of motion of a cosmetic applicator to enable movements that are necessary for cosmetic application. In some embodiments, the adapter 100 can be attached to a stand or carriage for further actions to be performed with a cosmetic held by the cosmetic applicator.

Figure 5B:
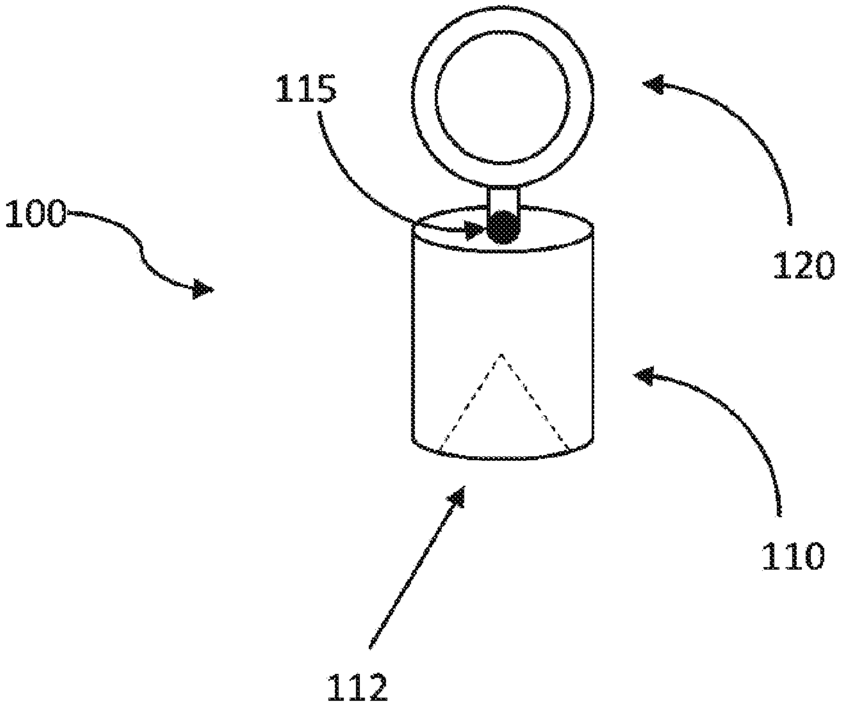
FIG. 5B is a transparent side view of the adapter, according to one embodiment.

FIG. 5B is a transparent side view of the adapter 100, according to one embodiment of the present disclosure. The adapter body 110 can be shaped approximately as a right cylinder. A first end of the adapter can be attached to one end of a motion stabilizer. The motion stabilizer can be a cylindrical rod forming a handle for a user to grasp. The first end can also be referred to hereinafter as a bottom end or a base of the adapter. The bottom end of the adapter body 110 can include at least one magnet, wherein the at least one magnet can be attracted to and attach to a magnet in the motion stabilizer. The bottom end of the adapter body 110 can include additional physical structures that can align, guide, and fix the adapter to the motion stabilizer. In one embodiment, the bottom end of the adapter body 110 can form a chamber 112, as illustrated in the transparent view of FIG. 5B. The chamber can be a hollow area within the body of the adapter 110 that is fully contained by the walls of the adapter 110. The chamber 112 can be approximately conical in shape. In one embodiment, the cutout can be cylindrical. The chamber 112 can be configured to fit over a projection on one end of the motion stabilizer. The chamber 112 can be used to align and guide the attachment of the cosmetic applicator to the motion stabilizer. The fit of the chamber 112 over and around the projection on the end of the motion stabilizer limits lateral motion that would misalign the cosmetic applicator and the motion stabilizer. It can be easier for a user to align the chamber 112 over the end of the motion stabilizer than it would be for the user to align the edges of the circular face of the adapter with the edges of the circular face of the motion stabilizer. The chamber 112 can have rotational symmetry such that the cutout can be placed over the end of the motion stabilizer in any orientation or at any degree of rotation around the axis of the chamber 112. In one end, a magnet can be fixed at the tip of the chamber, inside the body of the adapter. The magnet at the tip of the cutout can be attached to a magnet at the tip of the projection on the end of the motion stabilizer.

The cosmetic holder 120 can be located at a second end of the cosmetic applicator. In one embodiment, the cosmetic holder 120 can be a ring, wherein a cosmetic tool or product can be inserted into the ring. Many cosmetic tools, such as mascara wands, lipstick applicators, concealer applicators, and cosmetic pencils, are approximately cylindrical. In one embodiment, the ring can secure the cosmetic tools at the widest part of the tool. A ring-shaped holder can also hold cosmetic tools of varying shapes, such as cuboids. In one embodiment, the cosmetic holder 120 can include one or more projections along the inner wall of the holder and extending outward into the center of the holder. Contact and friction between the one or more projections and an inserted cosmetic tool can result in a more secure grip or hold of the cosmetic holder around the inserted cosmetic tool. In some embodiments, the inner wall of the cosmetic holder 120 can be lined with a material that can improve the grip or hold of the cosmetic holder around the inserted cosmetic tool. The improved grip can be a result of a material property, such as a coefficient of friction or a material deformation. For example, the inner wall can be lined with rubber or silicon. In one embodiment, the lining material can be a textured material with grooves, ridges, bumps, or similar features that prevent movement or slippage of the cosmetic tool once it is inserted into the cosmetic holder 120.

Various cosmetic holder configurations are compatible with the cosmetic applicator 100. In one implementation, the holder can be an open ring or a C-shaped holder. In one embodiment, the holder can be a loop, wherein the ends of the loop can overlap. In one embodiment, the holder can be one or more coiled loops. In one embodiment, the cosmetic holder 120 can be a tube or sheath forming a chamber inside the tube, wherein a cosmetic tool or product can be inserted into the chamber. In one embodiment, the tube can be closed on one end to contain a cosmetic tool or product in the chamber. In one example, the tube can be approximately cylindrical. In one example, the sheath can be a partial cylinder, such as a half-cylinder that does not wrap fully around the inserted cosmetic. In one embodiment, the size of the cosmetic holder 120 can be modified. For example, the cosmetic holder 120 can be a round holder, wherein the diameter of the holder can be modified to accommodate different cosmetic tools. A pushing force on a point along the outside of the holder can compress the holder to that of a smaller diameter. A pulling force on a point along the inside of the holder can expand the holder to that of a larger diameter. In one embodiment, the force can be applied at a single point along the holder to enable one-handed modification of the holder diameter. In one implementation, a user can be provided with a number of cosmetic holders, wherein each cosmetic holder has different dimensions or shapes for different cosmetic tools or products. A cosmetic holder 120 can be removed from the adapter body 110 and replaced with another of suitable configuration.

In one embodiment, the cosmetic holder 120 can be attached to the adapter body 110 with a joint 115, such as a ball joint. The ball joint can enable movement of the cosmetic holder 120 relative to the adapter body 110. For example, the cosmetic holder 120 can be rotated in place or can pivot to form an angle with the adapter body 110. The joint can be configured for continuous motion of the cosmetic holder 120 or for discrete steps of movement. According to some embodiments, the motion of the cosmetic holder 120 can be constrained. For example, the adapter 110 can form a walled channel, wherein the joint is disposed inside the walled channel. The walls of the channel can constrain movements of the joint and/or the cosmetic holder 120. In one embodiment, the joint 115 can be a motorized component. The cosmetic holder 120 can move as a result of the motorized component without requiring external force from a user.

Figure 5C:
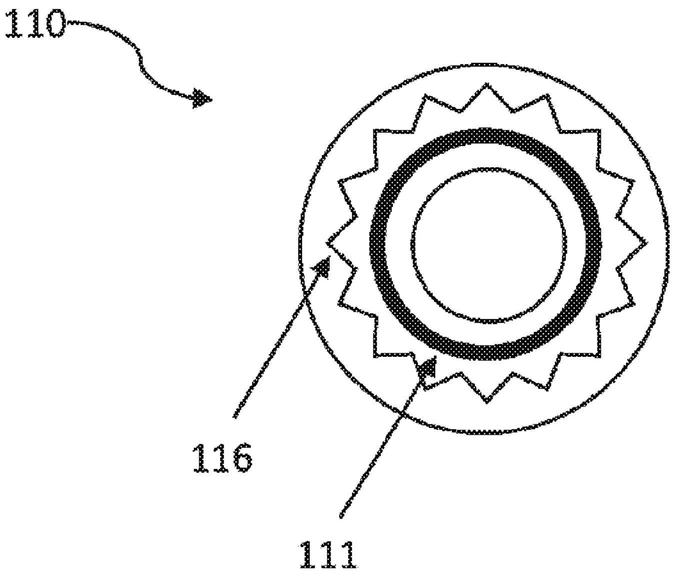
FIG. 5C is a view of the bottom face of the adapter body, according to one embodiment.

FIG. 5C is a view of the bottom face of the adapter body 110, according to one embodiment of the present disclosure. The bottom face of the adapter body 110 can be approximately a circle given that the adapter is a right cylinder. A magnet 111 can be disposed on the bottom face of the adapter. In one embodiment, the magnet 111 can be a uniformly ring-shaped magnet, as illustrated in FIG. 5C. For example, the magnet 111 can have the shape of a washer. The ring-shaped magnet 111 can be attracted to and attach to a magnet disposed along the circumference of one end of the motion stabilizer. In some embodiments, the adapter body 110 can be attached to the motion stabilizer in any orientation because of the ring-shaped magnet 111. The adapter body 110 can be attached to the motion stabilizer with any rotation of the adapter 100 around the central axis of the adapter. In one embodiment, the adapter 100 can be a universal adapter and can attach a magnetic end of the motion stabilizer in any orientation regardless of the positioning and/or polarity of magnets at the end of the motion stabilizer. Any portion of the ring-shaped magnet 111 at the base of the adapter can contact the magnets on the motion stabilizer to attach the adapter to the motion stabilizer.

The ring-shaped magnet 111 of the present disclosure presents an advantage over traditional adapters for motion stabilizer. For example, certain motion stabilizers can include two magnets located diametrically opposite to each other on a circular face of the motion stabilizer. Most traditional adapters include two magnets at the base for attachment to a motion stabilizer. The adapter can only be attached to the motion stabilizer if the two magnets on the motion stabilizer align with the two magnets in the same position on the adapter. In some implementations, the polarity of the magnets on the motion stabilizer can also differ such that each magnet on the motion stabilizer will only be attracted to one of the two magnets on the adapter. The limitations on the orientation of the traditional adapter can pose issues for users attempting to attach the adapter to the motion stabilizer. For example, users may lack the precision of movement needed to align the magnets as needed for attachment. In addition, the limitations on the orientation of the traditional adapter means that the orientation of the tool or instrument that is held by the applicator is also limited. When applying cosmetic products to or near the face, it can be desired that the applicator can be fixed at various angles and orientations or that the orientation of the applicator can be adjusted. For example, certain mascara wands are curved. The mascara wand should contact the eyelashes such that the curvature of the wand conforms to the curvature of the eye. It can be very difficult to achieve this position if the adapter holding the mascara wand can only be attached to the motion stabilizer in one orientation, as with traditional adapters with a limited number of magnets in set positions. In contrast, an adapter with a ring-shaped magnet, as in FIG. 5C, can be attached to the motion stabilizer in any orientation. The adapter can be rotated until the mascara wand, or any other cosmetic tool, is in a desired orientation for application and then attached to the motion stabilizer with contact between the ring-shaped magnet and any magnets disposed on the face of the motion stabilizer. The motion stabilizer can be maneuvered in various positions while the attached applicator and cosmetic also move. For example, the orientation of the attached applicator and the cosmetic can change as the user applies the cosmetic. The attachment of the applicator to the motion stabilizer without orientation expands the range of movement of the attached cosmetic.

In one embodiment, the adapter body 110 can include a ring of gears, teeth, or similar alignment structures 116. The alignment structures 116 can be located at the base of the adapter and can be concentric with the ring-shaped magnet 111. In one embodiment, the alignment structures can be located along the inner wall of the cutout at the bottom end of the adapter. In some embodiments, the alignment structures 116 can fit into or interlock with corresponding alignment structures on the motion stabilizer when the adapter is attached to the motion stabilizer. The alignment structures 116 can limit the rotation of the cosmetic applicator once the adapter has been attached to the motion stabilizer. Certain motion stabilizers can rotate in order to counteract any rotational force applied to the motion stabilizer so that an attachment to the motion stabilizer (such as the cosmetic applicator) remains steady. The “anti-rotation” mechanism can be useful for users who experience sudden, involuntary movements while holding the motion stabilizer. In one embodiment, the alignment structures 116 can be a ring of raised nubs or teeth-like structures that can fit into corresponding grooves or receptacles at the end of the motion stabilizer that is attached to the base of the adapter. In one embodiment, the alignment structures 116 can be a ring of recessed structures or a combination of raised and recessed structures that can fit into corresponding raised and/or recessed structures at the end of the motion stabilizer. The fitting of the alignment structures 116 into complementary structures at the end of the motion stabilizer can fix the cosmetic applicator in place when the adapter has been attached to the motion stabilizer. Any rotation of the motion stabilizer in order to counteract involuntary user movement will thus be carried through to the cosmetic applicator to maintain the orientation of the cosmetic applicator once the cosmetic applicator is attached to the motion stabilizer.

The alignment structures 116 can provide a range of discrete orientations at which the adapter can be attached to the motion stabilizer. For example, the adapter can only be attached to the motion stabilizer when each of the alignment structures 116 of FIG. 5C is aligned with a corresponding recessed structure in the motion stabilizer. If the alignment structures 116 are not aligned with and sitting in the recessed structures, the adapter will not be properly attached to the motion stabilizer. However, the symmetry of the repeated alignment structures 116 can still enable the attachment of the adapter at a number of rotations (e.g., 10+ rotational options) for easy attachment.

Figure 5D:
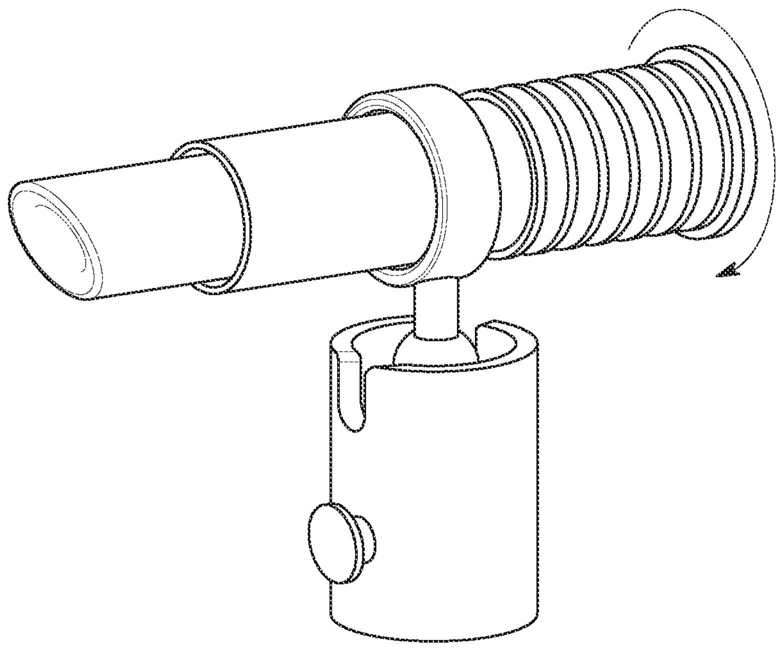
FIG. 5D shows how the adapter holds a specific cosmetic applicator, according to an embodiment.

FIG. 5D shows how the adapter 100 holds a specific cosmetic applicator, such as a lipstick applicator within the cosmetic holder 120. While a lipstick applicator is shown, the cosmetic holder can hold numerous examples of applicators, such as mascara applicators and nail polish applicators as other examples. In contrast to the adapter 1105 of FIG. 1, it can be seen that the cosmetic holder 120 holds the applicator at perpendicular angle to the handle of the motion stabilizer 150. This provides a more relaxed and ergonomic hand position for the user when using the cosmetic applicator.

Figure 6A:
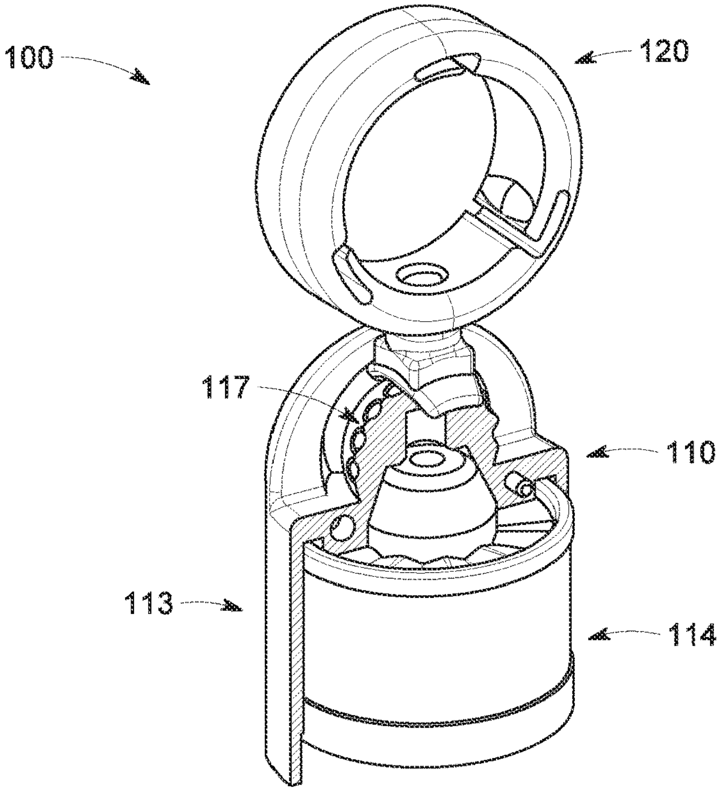
FIG. 6A is an illustration of the adapter 100 with a cutaway view of the adapter body 110, according to one embodiment.

FIG. 6A is an illustration of the adapter 100 with a cutaway view of the adapter body 110, according to one embodiment of the present disclosure. In one embodiment, the adapter body 110 can include an outer shell 113, wherein the outer shell 113 encloses an inner body 114. The inner body 114 can be attached to a motion stabilizer via the magnetic attachment described herein with reference to FIG. 5C. In one embodiment, the cosmetic holder 120 can be attached to the outer shell 113. The attachment of the cosmetic holder 120 to the outer shell 113 can enable movement of the cosmetic holder 120 that is independent of the movement of the inner body or the motion stabilizer. The attachment of the cosmetic holder 120 to the outer shell 113 can be enclosed within the adapter body 110. In one embodiment, the cosmetic holder 120 can be attached to the outer shell 113 along a series of detents in the outer shell. The detents can be, for example, a series of indentations, grooves, teeth, or the like, such as the indented structures 117 of FIG. 6A. The position of the cosmetic holder 120 can change by moving the cosmetic holder 120 linearly along the series of detents, such that the cosmetic holder 120 can be fixed in place at each of the detent structures 117. In one embodiment, the base of the cosmetic holder 120 can include a projection that fits into each of the detent structures 117. The projection can snap into place when positioned at or against each of the detent structures 117 to temporarily lock the cosmetic holder 120 into an angled position within a single plane. The plane of the face (opening) of the cosmetic holder 120 can stay the same while the angular position of the cosmetic holder 120 can be adjusted. A force can be applied by a user to position the cosmetic holder 120 at any of the detent structures 117. The cosmetic holder 120 can thus be angled relative to the central axis of the adapter body 110 and the attached motion stabilizer. In one embodiment, the cosmetic holder 120 can be attached to the adapter body 110 with a 2-axis adapter. The angle of the cosmetic holder 120 can be adjusted as described with reference to the detent structures 117. Additionally or alternatively, the plane of the opening of the cosmetic holder 120 can also be adjusted by a rotation of the cosmetic holder 120 for 2-axis movement. For example, the cosmetic holder 120 can rotate axially at or near the point of attachment to the adapter body 110. In one embodiment, the rotation of the cosmetic holder 120 can be modulated with detents or similar structures to provide a number of fixed rotational positions of the cosmetic holder 120. For example, the cosmetic holder 120 or the adapter body 110 can include an internal gear or ratcheting structure, wherein the cosmetic holder 120 can be rotated a number of degrees to engage the teeth of the internal gear. The cosmetic holder 120 can be temporarily locked in a rotational position when the teeth are engaged.

Figure 6B:
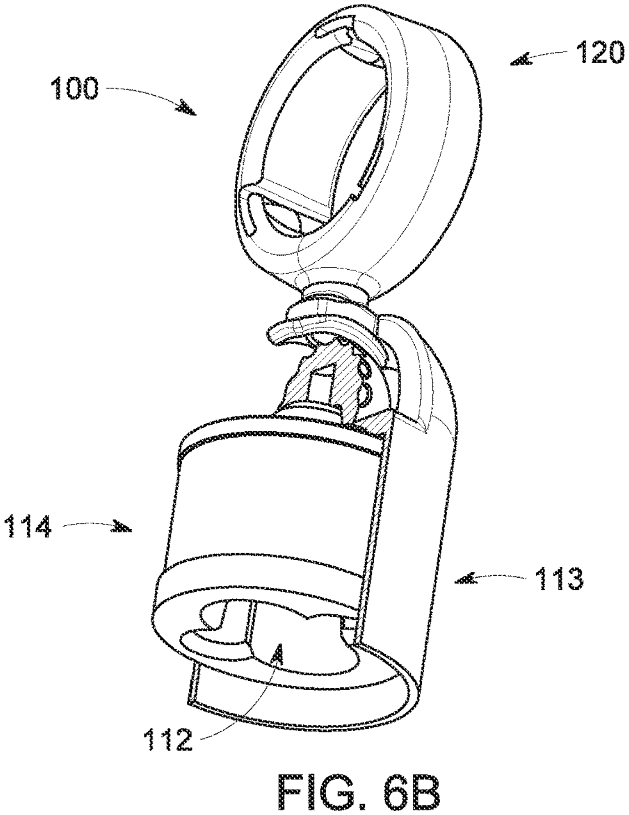
FIG. 6B is a side view of the adapter with a cutaway view of the adapter body, according to one embodiment.

FIG. 6B is a side view of the adapter 100 with a cutaway view of the adapter body 110, according to one embodiment of the present disclosure. The inner body 114 of the adapter body 110 can form the chamber 112, as has been described herein. Various shapes and dimensions of the chamber 112 are compatible with the present adapter 100. In one embodiment, the outer shell 113 can extend past the end of the inner body 114. The outer shell 113 can surround the attachment point of the adapter 100 to a motion stabilizer or other compatible structure and can prevent the adapter 100 from being displaced from the attached structure. In some embodiments, the magnetic ring can be formed at the base of the inner body 114.

Figure 6C:
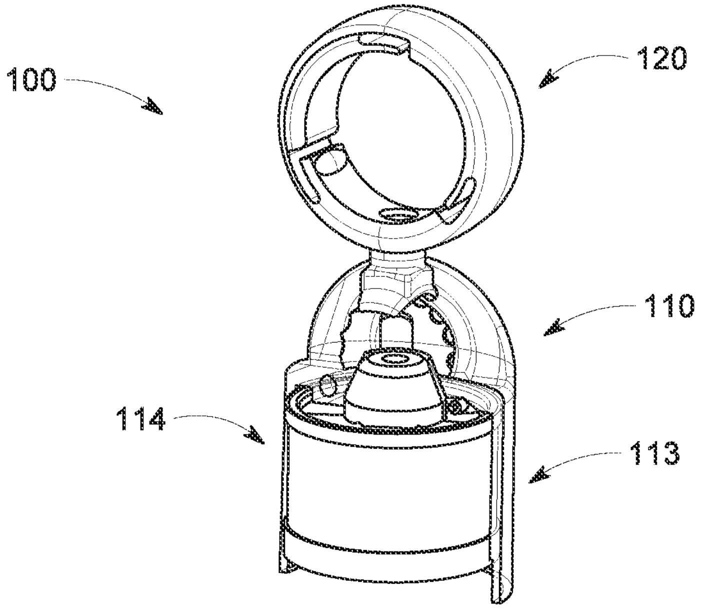
FIG. 6C is a transparent view of the outer shell of the adapter, according to one embodiment.

FIG. 6C is a transparent view of the outer shell 113 of the adapter 100, according to one embodiment of the present disclosure. The outer shell 113 can form a cavity surrounding the inner body 114. In one embodiment, the inner body 114 can rotate relative to the outer shell 113 while the outer shell 113 and/or the cosmetic holder 120 are fixed in place and do not rotate. For example, the inner body 114 can rotate in order to counteract an unintentional rotational movement of the motion stabilizer or the adapter 100. The rotation of the inner body 114 is not translated to the cosmetic holder 120 because the cosmetic holder 120 is not in contact with the inner body 114. Similarly, the fitting of the outer shell 113 around the inner body 114 can include a gap between the outer shell 113 and the walls of the inner body 114 so that the rotation of the inner body 114 is not translated to the outer shell 113.

Figure 6D:
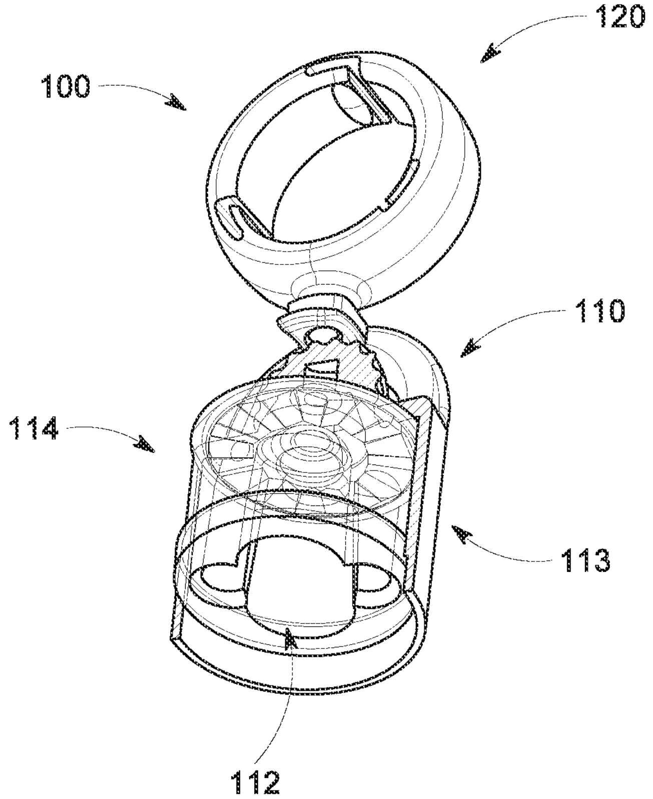
FIG. 6D is a transparent view of the inner body of the adapter, according to one embodiment.

FIG. 6D is a transparent view of the inner body 114 of the adapter 100, according to one embodiment of the present disclosure. The inner shell 114 can form the chamber 112, as has been described herein. The chamber 112 can extend to the top of the inner body. In one embodiment, the chamber 112 can be shaped as a central cylinder with two cylinders adjacent to the central cylinder, as illustrated in FIG. 6D. The shape of the chamber 112 and the symmetry of the chamber 112 can depend on the intended attachment to a motion stabilizer or other structure. In one embodiment, the shape of the chamber 112 can depend on the desired movement of the adapter 100. For example, an infinitely symmetrical chamber can be attached onto a motion stabilizer in any orientation and can remain stationary when the motion stabilizer rotates. In another example, a chamber with limited axes of symmetry can result in a fixed number of orientations at which the adapter can be attached to the motion stabilizer.

In one embodiment, the attachment of the cosmetic applicator to the motion stabilizer can activate at least one sensor to indicate that the adapter body 110 has been successfully attached to the motion stabilizer. The at least one sensor can be, for example, a Hall effect sensor that can detect and respond to the magnetic field produced by the adapter and/or the motion stabilizer. In one embodiment, the at least one sensor can be a pressure-activated sensor. Alternative sensors known to those of ordinary skill in the art can be compatible with the systems and apparatuses disclosed herein. In one embodiment, the at least one sensor can detect when the cosmetic applicator has not been attached to the motion stabilizer properly. For example, a Hall effect sensor can detect a partial magnetic field from the adapter with a magnitude that is less than an expected magnitude. The partial magnetic field can indicate that a portion of the ring-shaped magnet on the adapter is physically shielded or has failed to produce a magnetic field. In one embodiment, the data from the at least one sensor can be used to notify a user to inspect the cosmetic applicator or reattach the cosmetic applicator.

In one embodiment, the adapter 100 can include one or more sensors and/or an integrated circuit. The one or more sensors can include, but are not limited to, pressure sensors, light sensors, weight sensors, tension or force sensors, a Hall sensor, an accelerometer, a gyroscope, or the like. Data from the one or more sensors can be used to identify when a cosmetic has been inserted into or attached to the cosmetic applicator. In one embodiment, the data from the one or more sensors can be used to identify physical features of an attached cosmetic, such as a size, a shape, or a weight of the attached cosmetic. In one embodiment, the data from the one or more sensors can relate to a motion of the cosmetic applicator 100 or a motion of an attached component, such as the attached cosmetic or the motion stabilizer. In one embodiment, the data from the one or more sensors can be transmitted from the cosmetic applicator to a remote device, such as a server or a user device. In one embodiment, the cosmetic applicator can receive data, including instructions, from the same remote device or a second remote device. Further detail surrounding network In an embodiment, the system described above includes the functionality to auto-detect adapters to activate specific protocols to the motion stabilizer device 150. For instance, the motion stabilizer device 150 may perform auto detection of different adapters that are used for different cosmetics such as lipstick, mascara, etc. As soon as the adapter is connected to the handle of the motion stabilizer device 150, the handle will automatically recognize which style of adapter (for example, lipstick vs mascara) is attached and will load a specific set of protocols developed for that specific application.

Figure 7:
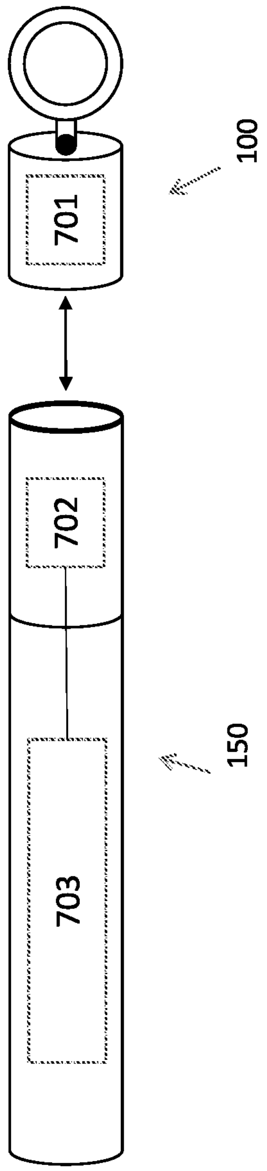
FIG. 7 shows a block diagram of the communicative hardware elements in the stabilizer device and the adapter, according to an embodiment.

FIG. 7 shows a block diagram of the communicative hardware elements in the stabilizer device 150 and the adapter. The adapter includes a communication interface 701 and the receiver portion of the stabilizer device includes a communication interface 702. The communication interfaces, in one example, is a near field communication (NFC) interface (where element 702 is a radiofrequency identification (RFID) reader configured to read an RFID tag 701). Furthermore, the receiver portion of the stabilizer device includes the hall effect sensor 704 described above. Thus, the RFID reader may be activated in response to the hall effect sensor 704 detecting insertion of the adapter 100. Alternatively, each of interfaces 701 and 702 operate as Bluetooth interfaces in another example, such as Bluetooth Low Energy (BLE) type interfaces.

The interface 702 in the receiver portion is connected to PCBA 703 that is coupled to or includes a memory 705 that stores different protocol information.

Once device 150 recognizes the adapter 100 that is present, it will receive information on the type of specific adapter it is based on information stored on the communication interface 701. The communication interface 702 then communicates the information to the PCBA 703, which stores specific protocols in the device software that target specific gestures and movements for the specific adapter connected (i.e. if lipstick adapter is attached, device will call on lipstick gesture protocols)

Figure 8:
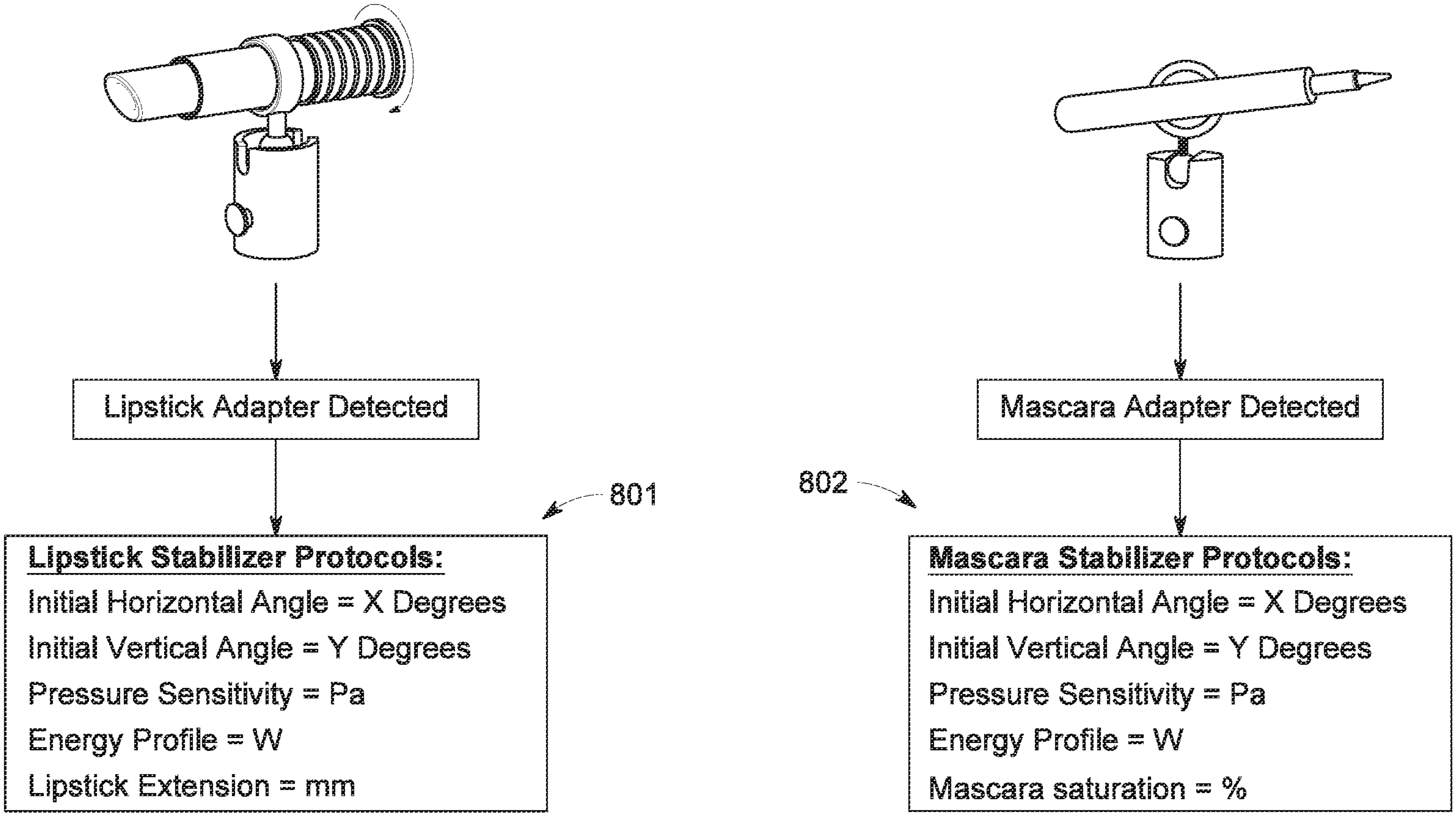
FIG. 8 shows different protocols for when the adapter has different cosmetic applicators, according to an embodiment.

For instance, as shown in FIG. 8, a first set of protocols 801 for a lipstick may include specific parameters initial angles of orientation of the stabilizer along with settings for pressure sensitivity, energy consumption, and initial lipstick extension. While a different second set of protocols 802 for a mascara may include different specific parameters initial angles of orientation of the stabilizer along with settings for pressure sensitivity, energy consumption, and mascara saturation.

There could be multiple adjustments to each protocol depending on the adapter and applicator. For example, with lipstick it is desired to remove the axial rotation of the adapter with respect to the handle since this can at times cause unwanted or unexpected movements for the user. It is also desired to limit the amount of flexion, and to create an initial "home position" as the hand holding position may be different for lipstick vs mascara. Additionally, it is desired to change the speed at which the motors move for mascara to be a bit slower so that there is less risk of unintended movements within close vicinity of the eyes. An example for additional lipstick protocol features are as follows.

Disable axial rotation of adapter relative to handle

Set motor speed to 100% for quickest possible adjustments

Flex adapter to initial "home" angular setting for best application orientation

Figure 9:
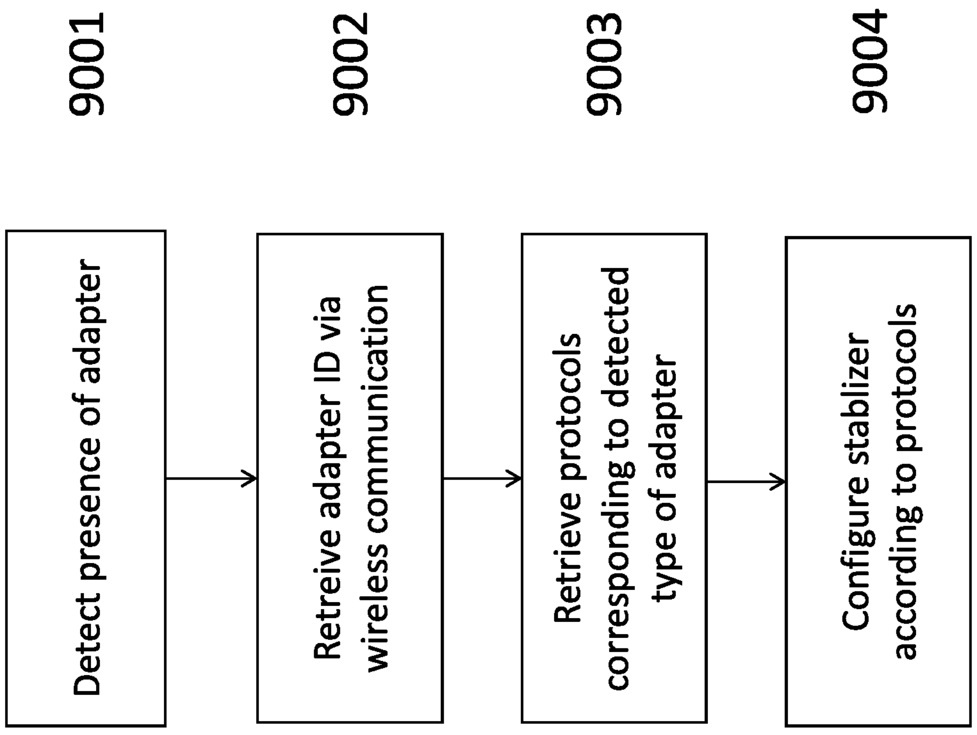
FIG. 9 shows a flowchart for performing the auto-detection.

FIG. 9 shows a flowchart for performing the auto-detection as discussed above. The steps are performed at the motion stabilizer device 150. In step 9001, the communication interface 702 detects the presence of the adapter 100. For instance, when the communication interface 702 is an RFID reader and the communication interface 701 is an RFID tag, these elements may perform an initial handshake before establishing a communication channel, as is understood in the art.

In step 9002, after a communication channel is established between the communication interfaces 701 and 702, the communication interface 701 transmits identification information to the communication interface 702. The identification information indicates the type of adapter as discussed above.

In step 9003, the communication interface 702 transmits the received identification information to the PCBA 703 that is onboard the stabilizer device, and the PCBA 703 retrieves the protocols stores on a local memory that correspond to the identified type of adapter.

In step 9003, the PCBA 703 controls configuration of the motion stabilizer device according to the stored protocols after it is detected that the adapter is attached to the motion stabilizer device.

With the above procedures, not only will the motion stabilizer device recognize an adapter is present, but it will recognize whether it is a specific adapter used for lipstick, mascara, or others. Once device recognizes the adapter that is present, it will call on specific protocols in the device software that target specific gestures and movements for the specific adapter connected (i.e. if lipstick adapter is attached, device will call on lipstick gesture protocols).

In one embodiment, the cosmetic holder 120 can be configured to rotate within the plane formed by the cosmetic holder 120 around the central axis of the cosmetic holder 120. The rotation of the cosmetic holder 120 can result in the rotation (turning) of a cosmetic tool inserted into the cosmetic holder 120. Rotation of an inserted cosmetic tool can be useful for certain cosmetic products that are extruded or applied via a rotational motion. Extrusion can refer to translation of a cosmetic product (e.g., a cosmetic formula) stored in a cosmetic tool towards an opening or applicator portion of the cosmetic tool so that the cosmetic product is exposed and can be applied to a user. Cosmetic products can also be retracted, e.g., translated away from the opening or applicator portion of the cosmetic tool. Examples of cosmetic products that can be extruded using rotation can include, but are not limited to, lipsticks and related lip products, concealers, cosmetic pencils, cosmetic brushes, etc. For example, a lipstick can include an inner tube inserted into a base. The inner tube can contain the lipstick product formed into a tip at a first end of the inner tube. The tip can be symmetrical (e.g., a bullet shape) or can be asymmetrical (e.g., a chisel tip). When the inner tube is rotated relative to the base (or vice versa), the lipstick product is extruded or retracted from an opening at the first end of the inner tube.

The rotation of the inner tube relative to the base can be achieved via a number of rotational actuations. In a first example, the inner tube can be stationary (fixed) while the base can be rotated in a first direction (clockwise) to extrude the lipstick. In a second example, the base can be stationary (fixed) while the inner tube can be rotated in a second direction opposite to the first direction to extrude the lipstick. In a third example, the base can be rotated in the first direction and the inner tube can be rotated in a second direction (counterclockwise) opposite to the first direction to extrude the lipstick. Similarly, the reversal of the relative directions can result in the lipstick formula being retracted.

In one embodiment, the cosmetic holder 120 can be configured to rotate an inserted cosmetic tool in order to open or close the cosmetic tool. For example, the cosmetic holder 120 can rotate a cap of a cosmetic product to unscrew the cap from a body of the cosmetic product. In one embodiment, the rotating cosmetic holder can be configured to open packaging surrounding a cosmetic tool or product. For example, cosmetics can be wrapped in plastic or be disposed inside a plastic casing. The packaging of a cosmetic can be difficult to open for a user with limited mobility, grip strength, or control of fine motor movement. The cosmetic holder 120 can apply rotational forces in order to open the packaging. For example, an eyeliner pencil can be wrapped in plastic packaging to prevent the cap of the pencil from being removed before the pencil is purchased. The plastic packaging can be a flexible plastic, wherein a twisting motion of the cap relative to the pencil can tear the plastic packaging. The broken packaging will lift up from the pencil and the cap and can be easily grasped and peeled off of the pencil.

In one implementation, the cosmetic holder 120 can be configured to rotate an inserted cosmetic tool while the cosmetic tool is in use. For example, a mascara wand can be rotated while the wand is in contact with a user's eyelashes in order to change the orientation of the wand, to maximize the amount of mascara product deposited by the wand, and/or to evenly distribute the mascara product from the wand. Similarly, a concealer wand can have an applicator that is dipped into the concealer product. It can be useful for the cosmetic holder to rotate the concealer wand during application in order to deposit all of the concealer product on the applicator onto the user's face. In another example, a lipstick with a chisel tip can be positioned for application so that the flat face of the chisel tip faces a user's lip. The chisel tip can be rotated by 180° for application to a top lip and a bottom lip. The rotation of a cosmetic tool via the cosmetic holder 120, as described herein, can depend on the type of cosmetic tool and the purpose of the rotation. The cosmetic holder 120, as illustrated in FIG. 5A, can also pivot around the joint 115 and can rotate while in a fixed position.

In one embodiment, the cosmetic holder 120 can be coupled to a rotatable gear, surface, shell, etc. that can rotate an inserted cosmetic tool. In one embodiment, the cosmetic holder 120 can be coupled to more than one rotational gear in order to provide more than one origin point of rotation for an inserted cosmetic tool. In one embodiment, a first portion of the cosmetic holder 120 can be configured to rotate in a first direction while a second portion of the cosmetic holder 120 can be configured to rotate in a second direction or can be stationary.

Figure 10B:
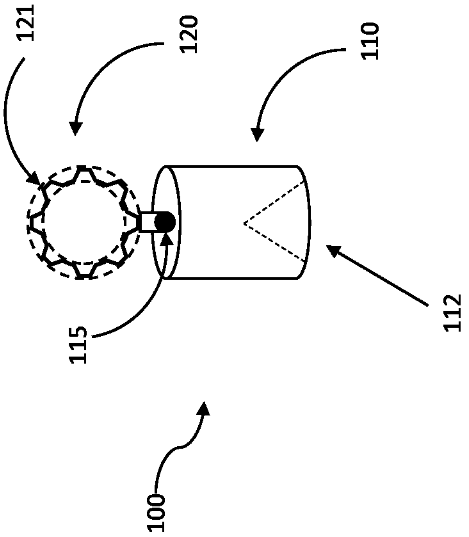
FIG. 10B is a view of an adapter including a concentric rotational gear.
Figure 10A:
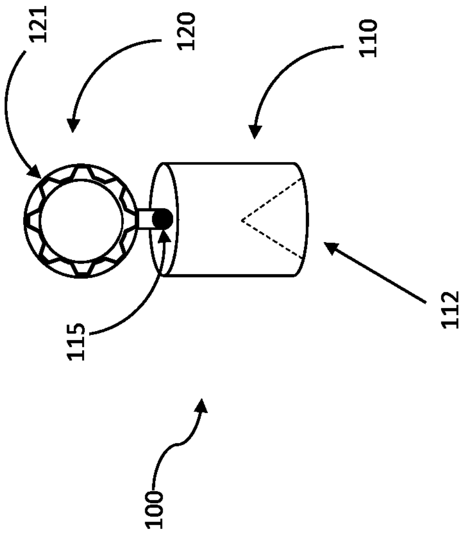
FIG. 10A is a view of an adapter including an in-line rotational gear.

FIG. 10A is an illustration of an adapter 100 including a rotational gear 121 and a cosmetic holder 120. In one embodiment, the rotational gear 121 can be an in-line gear. A first face of the in-line gear 121 can be coupled to a first face of the cosmetic holder 120. In one embodiment, the in-line gear 121 can form the first face of the cosmetic holder 120. The in-line gear 121 may or may not be in contact with the cosmetic holder 120. FIG. 10B is a transparent view of an adapter 100 wherein the rotational gear 121 is a concentric gear. A concentric gear 121 can be an internal gear provided inside the cosmetic holder 120. For example, when the cosmetic holder 120 is a ring, the concentric gear 121 can be located within the walls of the ring. An inserted cosmetic tool can be in contact with the inner wall of the cosmetic holder 120. The rotation of the concentric gear 121 can result in the rotation of the surrounding cosmetic holder 120. A shape of the rotational gear 121 (e.g., a ring gear with teeth) is provided in FIGS. 10A and 10B as a non-limiting example. In some embodiments, the teeth of the rotational gear 121 can be rounded, pointed, curved, etc. and can include inner teeth and/or outer teeth. In one embodiment, the rotational gear 121 can be a round disc without teeth. In some embodiments, the rotational gear 121 can be a rotatable sheath, such as a cylinder or half-cylinder. In one embodiment, the rotational gear 121 can rotate independently from the cosmetic holder 120. For example, the in-line gear 121 illustrated in FIG. 10A can rotate while the cosmetic holder 120 is fixed. An inserted cosmetic tool that is in contact with the inner surface of the in-line gear 121 can rotate along with the rotation of the in-line gear 121. An inner surface of the cosmetic holder 120 (e.g., a surface in contact with an inserted cosmetic tool) can be a smooth surface comprising a low-friction material so that an inserted cosmetic tool can rotate within the cosmetic holder 120.

Figure 11B:
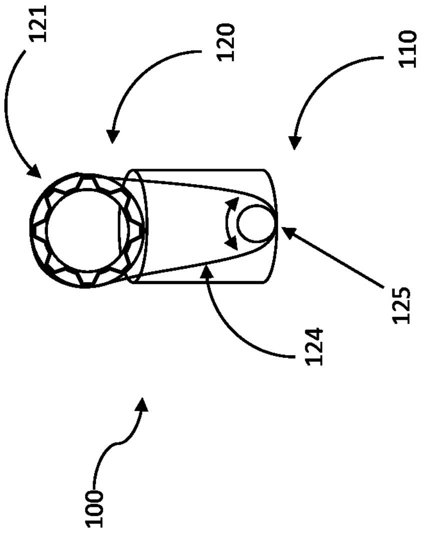
FIG. 11B is a view of an adapter including a rotational gear actuated by a belt system.
Figure 11A:
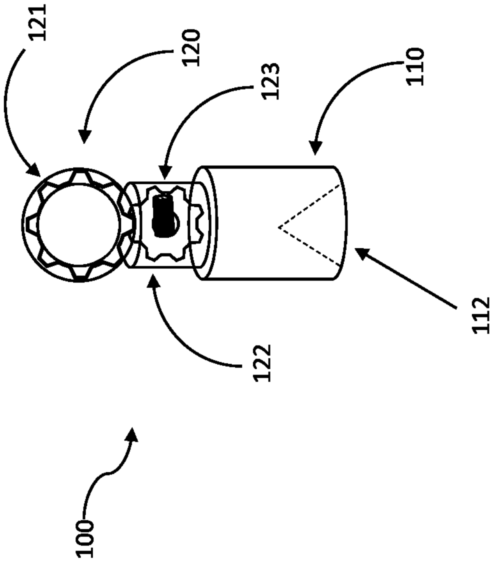
FIG. 11A is a view of an adapter including a rotational gear actuated by a geared system.

In one embodiment, a portion of the rotational gear 121 can be exposed to a rotator or actuator, wherein the actuator is configured to rotate the rotational gear 121. In one embodiment, the rotational gear 121 can be actuated by a motor. The motor can provide torque for rotation of the rotational gear 121. In one embodiment, the motor can be in the cosmetic holder 120, the adapter body 110, or the motion stabilization handle 150. FIG. 11A is an illustration of a rotational gear 121 driven by a geared system, wherein the geared system includes at least one driver gear 122. In one embodiment, a motor 123 can drive the rotation of the driver gear 122. The motor 123 can be an electric motor, such as a direct current (DC) motor that can be powered by the power source 1301 of the motion stabilization device 150. The motor 123 can form the gear axle of the driver gear 122 or can be coupled to a gear axle of the driver gear 122. When power (current) is supplied to the motor 123, the gear axle of the driver gear 122 can spin, causing the driver gear 122 to rotate. The rotational gear 121, which is coupled to the driver gear 122 via the gear teeth, can rotate as a result of the rotation of the driver gear 122. In one embodiment, the driver gear can be coupled to the rotational gear 121 within the adapter body 110. The motor 123 can be coupled to the rotational gear 121 via any number of intermediate driver gears, including gears (e.g., bevel gears) for rotation around non-parallel axes. Thus, the continuous rotational motion of the motor and gear axle can drive a discrete rotational motion of the rotational gear 121.

In one embodiment, the rotational gear 121 can be actuated by a belt drive. FIG. 11B is an illustration of a belt-driven actuator system. A belt (band) 124 can wrap around the circumference of the rotational gear 121. The movement of the belt along the circumference of the rotational gear can translate to rotation of the rotational gear 121. The movement of the belt can be driven by a second gear 125, a motor, etc. located in the adapter body 110 or in the motion stabilization handle 150. Inventors: Please provide additional information on how the gears can be actuated or rotated, if applicable.

In one implementation, a user can use the cosmetic holder 120 to extrude lipstick in a tube. The tube of lipstick can be inserted into a ring-shaped cosmetic holder 120. The user can hold the base of the tube so that the base is stationary. The rotational gear 121 can then rotate the lipstick tube relative to the stationary base so that the lipstick product is extruded. The use of the rotational gear 121 can be helpful for a user who cannot grip the base of the tube and rotate the body of the tube at the same time. In one embodiment, the cosmetic holder 120 can include more than one rotational gear 121. For example, the cosmetic holder 120 can be a cylindrical tube including a first rotational gear at a first end of the cylindrical tube and a second rotational gear at a second (opposing) end of the cylindrical tube. A first part of the cosmetic holder 120 surrounding or coupled to the first rotational gear can move independently of a second part of the cosmetic holder 120 surrounding or coupled to the second rotational gear. The rotational gears can be in-line gears or concentric gears, as described with reference to FIGS. 10A and 10B.

Figure 12:
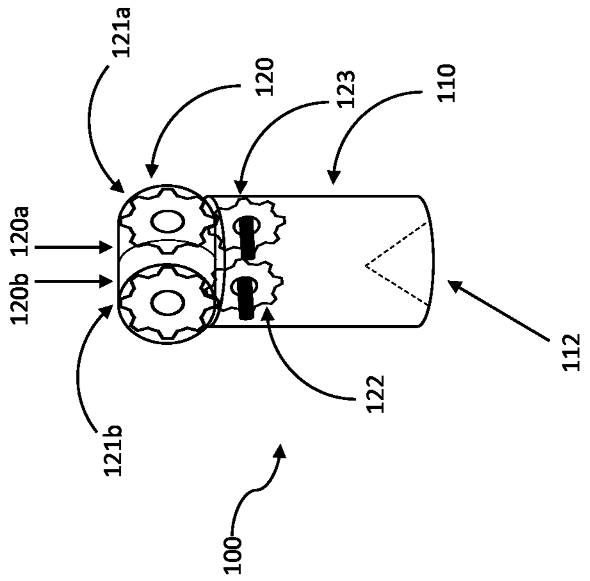
FIG. 12 is a view of an adapter including a first rotational gear and a second rotational gear.

FIG. 12 is an illustration of a cosmetic holder 120 with two rotational gears 121*a*, 121*b*, according to one example. The first rotational gear 121*a* can be coupled to a first portion 120*a* of the cosmetic holder, and the second rotational gear 121*b* can be coupled to a second portion 120*b* of the cosmetic holder. The first portion 120*a* and the second portion 120*b* can be in contact with each other, e.g., at a seam, or can be physically separate from each other. The first rotational gear 121*a* can rotate the first portion 120*a* of the cosmetic holder, and the second rotational gear 121*b* can rotate the second portion 120*b* of the cosmetic holder. The driver gear 122 can include a separate driver gear for each of the first rotational gear 121*a* and the second rotational gear 121*b*. The motor 123 can include a separate motor for each of the first rotational gear 121*a* and the second rotational gear 121*b*.

The first rotational gear 121*a* and the second rotational gear 121*b* can rotate in tandem or independently. For example, the first rotational gear can be fixed, and the second rotational gear can rotate. The portion of the inserted cosmetic tool that is in contact with the first portion 120*a* will be fixed, while the portion of the inserted cosmetic tool that is in contact with the second portion 120*b* will rotate. As an example, the inserted cosmetic tool can be a tube of lipstick. The base of the lipstick can be in contact with the first portion 120*a* of the cosmetic holder, while the tube of lipstick containing the product can extend from the base and be in contact with the second portion 120*b* of the cosmetic holder. The base of the lipstick can be held in a stationary position by the first (stationary) rotational gear 121*a*, while the tube of lipstick is rotated relative to the base by the second rotational gear 121*b*. The lipstick product can then be extruded or retracted without the user needing to stabilize or touch any part of the lipstick. In one example, the first rotational gear can rotate while the second rotational gear is stationary, or the first and the second rotational gear can rotate in opposing directions.

Parameters of rotation of the cosmetic holder 120 can include, but are not limited to, a speed of rotation, a direction of rotation (e.g., clockwise or counterclockwise), an amount of rotation (e.g., a number of degrees), a step size (e.g., the smallest number of degrees that the cosmetic holder 120 can rotate), and which rotational gear part rotates. It can be beneficial for the parameters of rotation to be adjustable for a given cosmetic holder 120 so that the cosmetic holder can be used for a variety of functions. For example, lipstick can be extruded from a tube by rotating the tube by a number of degrees. A mascara wand can be rotated during application by a number of degrees. The amount of rotation needed for the two functions can vary and be different in range (e.g., 360° to extrude lipstick and 180° to apply mascara). In addition, the speed of rotation can vary for different functions. A cosmetic tool can be rotated more slowly during cosmetic application when compared to a rotation used to extrude or retract a product from the cosmetic tool. The parameters of rotation can depend on the power supplied to an actuator (e.g., a motor) of the rotational gear 121.

In one embodiment, a pushbutton, switch, or similar electrical connector can control the actuation of the rotational gear. The pushbutton or switch can be provided on the base or side of the motion stabilization device 150 and can be electrically connected to the circuitry of the motion stabilization device 150. Actuating a pushbutton or switch can result in current being supplied to a motor in order to rotate the rotational gear. In one example, a user can control the rotation of the rotational gear by pushing a pushbutton a set number of times, wherein each push results in the rotational gear rotating by a single step (e.g., a set number of degrees). In one embodiment, when the pushbutton is held down, the current can be continuously supplied to the motor and the rotational gear can continue rotating in steps until the pushbutton is released. In one embodiment, a pushbutton or switch can modify the voltage supplied to the actuator (e.g., the motor) in order to modify the speed of rotation. For example, pushing a pushbutton can cycle through a number of voltages that can be supplied to the motor to modify the speed of rotation.

In one embodiment, the actuator can rotate the rotational gear with certain parameters of rotation based on a type of rotation or function. For example, the actuator can rotate the rotational gear a set number of degrees at a set speed based on the rotation or function. In one embodiment, the circuitry of the motion stabilizer device 150 or the adapter 100 (e.g., a PCBA 703) can access and execute one or more rotation protocols, wherein a rotation protocol can refer to an actuation of the rotational gear according to one or more parameters. The circuitry can access the one or more rotation protocols according to the method described herein with reference to FIG. 8 and FIG. 9. For example, the PCBA can execute a rotation protocol for extruding lipstick from a tube. When the protocol is executed, a set voltage and current can be supplied to a motor for a set amount of time in order to rotate the rotational gear by a number of degrees and at a speed corresponding to the extrusion of lipstick. In another example, the PCBA can execute a rotation protocol for applying mascara. When the protocol is executed, a set voltage and current can be supplied to a motor for a set amount of time in order to rotate the rotational gear by a number of degrees and at a speed corresponding to mascara application. The speed of rotation (voltage) for mascara application can be lower than the speed of rotation (voltage) for lipstick extrusion, while the amount of time during which the actuator is powered can be longer for mascara application than for lipstick extrusion. In one embodiment, a rotation protocol can be executed via a pushbutton, switch, or similar mechanical actuator on the cosmetic applicator. In one embodiment, a rotation protocol can be accessed and/or executed based on sensor data collected by the motion stabilizer device 150 or the adapter 100. For example, the sensor data described herein can be used to identify a type of cosmetic tool that has been inserted into the cosmetic holder. The circuitry of the adapter 100 can be configured to execute a rotation protocol corresponding to the identified cosmetic tool.

As an illustrative example, a rotational protocol can correspond to application of lipstick. The circuitry of the motion stabilization device can identify that a tube of lipstick has been inserted into the cosmetic holder 120 based on sensor data collected by the motion stabilization device 150 and/or the cosmetic adapter 100. The cosmetic holder 120 can include a first rotational gear and a second rotational gear, as illustrated in FIG. 12. The rotational protocol corresponding to a tube of lipstick can include a first step in which the first rotational gear is stationary, and the second rotational gear is actuated by a motor to rotate clockwise at a set speed for a set number of degrees (e.g., 360°). The rotation of the tube of lipstick by the second rotational gear relative to the first rotational gear can result in a tip of the lipstick being extruded from the opening of the tube. The motor can then stop rotating the second rotational gear while the user applies the lipstick to one of two lips (top lip or bottom lip). In one embodiment, the circuitry of the motion stabilization device 150 and/or the cosmetic adapter 100 can determine that the lipstick has been applied to the one of two lips. For example, sensor data from pressure sensors in the cosmetic adapter 100 can indicate that the lipstick is no longer being pressed against a surface (the user's lip). The rotational protocol corresponding to the tube of lipstick can further include a second step in which the first rotational gear and the second rotational gear rotate in tandem in order to rotate the inserted lipstick by 180°. The rotation by 180° can result in a change in the orientation of the tip of the lipstick. In this manner, the user can apply the lipstick to a second of two lips with a desired side of the lipstick tip. The rotational protocol can further include a third step in which the first rotational gear is stationary, and the second rotational gear is actuated by a motor to rotate counterclockwise at the set speed for a set number of degrees (e.g., 360°). The rotation of the tube of lipstick by the second rotational gear in a counterclockwise direction can result in the lipstick tip being retracted into the tube. In one embodiment, the third step can be executed automatically when the sensor data from the pressure sensors indicate that the lipstick is no longer being pressed against a surface (the user's lip). The cosmetic adapter 100 can thus automate each motion that is needed to apply the lipstick, including rotating the lipstick to one or more orientations, in a rotation protocol.

In one embodiment, the circuitry of the motion stabilization device 150 and/or the cosmetic adapter 110 can store or access a position, orientation, configuration, or rotation that is associated with a cosmetic tool or product. The stored position can be a preferred position of the cosmetic tool or can be a most recent position of the cosmetic tool. For example, the circuitry can store a number of rotations or degrees of rotation associated with a tube of lipstick. The degrees of rotation can correspond to an amount of the lipstick that is extruded for application. The amount of lipstick can be a preference of a user, which can be set by a user as an input and accessed by the communication interface 702 of the motion stabilization device. In one embodiment, the amount of lipstick corresponding to the degrees of rotation can be an amount that is at least the same as a previously extruded amount. For example, the circuitry 703 can access a number of degrees that the lipstick was rotated to extrude the product in a most recent usage. Given that the product is gradually used up over time, the cosmetic holder 120 can rotate the lipstick by at least the same amount in a next usage. In one embodiment, the degrees of rotation can increase by a constant or variable amount with each usage to ensure that enough product is extruded with each usage. The setup and application of a cosmetic tool can thus be automated and repeatable to minimize interactions by a user while maintaining and meeting user preferences.

Obviously, numerous modifications and variations of the present invention are possible in light of the above teachings. It is therefore to be understood that within the scope of the appended claims, the invention may be practiced otherwise than as specifically described herein.

The invention claimed is:

1. A cosmetic securement device for stabilization of a cosmetic applicator, comprising:

a motion stabilizer handle;

an adapter coupled to a first end of the motion stabilizer handle and including a ring-shaped component configured to hold the cosmetic applicator; and at least one rotational gear coupled to the adapter, the at least one rotational gear being concentric with the ring-shaped component, wherein a rotational axis of the at least one rotational gear is a central axis of the ring-shaped component, wherein the motion stabilizer handle includes at least one sensor configured to detect a movement caused by a user, circuitry configured to determine a compensation movement to offset the detected movement, and at least one motion generation device configured to control a motion of the cosmetic applicator according to the determined compensation movement, wherein the adapter is configured to hold a plurality of types of cosmetic applicators, and wherein the at least one rotational gear is configured to rotate the cosmetic applicator held by the adapter.

2. The device according to claim 1, wherein each of the at least one rotational gear is configured to rotate independently of each other.

3. The device according to claim 1, wherein the at least one rotational gear is coupled to a face of the ring-shaped component.

4. The device according to claim 1, wherein the at least one rotational gear is embedded in the ring-shaped component.

5. The device according to claim 1, wherein the at least one rotational gear is actuated by an electric motor embedded in the cosmetic securement device.

6. The device according to claim 5, wherein the electric motor is coupled to the at least one rotational gear via at least one driver gear.

7. The device according to claim 5, wherein the electric motor is coupled to the at least one rotational gear via a shared belt.

8. The device according to claim 5, wherein the at least one rotational gear is actuated by the electric motor in response to actuation of a pushbutton or a switch embedded in the cosmetic securement device.

9. A cosmetic securement device for stabilization of a cosmetic applicator, comprising:

a motion stabilizer handle;

an adapter coupled to a first end of the motion stabilizer handle, the adapter including a cylindrical sheath configured to hold the cosmetic applicator; and at least one rotational gear coupled to the adapter, wherein the motion stabilizer handle includes at least one sensor configured to detect a movement caused by a user, circuitry configured to determine a compensation movement to offset the detected movement, and at least one motion generation device configured to control a motion of the cosmetic applicator according to the determined compensation movement, wherein the adapter is configured to hold a plurality of types of cosmetic applicators, wherein the at least one rotational gear is configured to rotate the cosmetic applicator held by the adapter, and wherein the at least one rotational gear includes a first rotational gear coupled to a first section of the cylindrical sheath and a second rotational gear coupled to a second section of the cylindrical sheath.

10. The device according to claim 9, wherein the at least one rotational gear is concentric with the cylindrical sheath and wherein a rotational axis of the at least one rotational gear is a central axis of the cylindrical sheath.

11. The device according to claim 10, wherein the at least one rotational gear is coupled to a face of the cylindrical sheath.

12. The device according to claim 10, wherein the at least one rotational gear is embedded in the cylindrical sheath.

13. The device according to claim 9, wherein each of the at least one rotational gear is configured to rotate independently of each other.

14. The device according to claim 9, wherein the first section of the cylindrical sheath and the second section of the cylindrical sheath are configured to rotate independently of each other.

15. A cosmetic securement device for stabilization of a cosmetic applicator, comprising:

a motion stabilizer handle;

an adapter coupled to a first end of the motion stabilizer handle; and at least one rotational gear coupled to the adapter, wherein the motion stabilizer handle includes at least one sensor configured to detect a movement caused by a user, circuitry configured to determine a compensation movement to offset the detected movement and a rotation of the at least one rotational gear based on a type of the cosmetic applicator, and at least one motion generation device configured to control a motion of the cosmetic applicator according to the determined compensation movement, wherein the adapter is configured to hold a plurality of types of cosmetic applicators, wherein the at least one rotational gear is configured to rotate the cosmetic applicator held by the adapter, wherein the at least one rotational gear is concentric with the cylindrical sheath, and wherein a rotational axis of the at least one rotational gear is a central axis of the cylindrical sheath.

16. The device according to claim 15, wherein the circuitry is configured to determine a speed of the rotation and an amount of rotation of the at least one rotational gear based on the type of the cosmetic applicator.

17. The device according to claim 15, wherein the at least one rotational gear is actuated by an electric motor and wherein the circuitry is configured to control power to the electric motor.

* * * * *